(12) United States Patent
Heiner et al.

(10) Patent No.: US 8,003,330 B2
(45) Date of Patent: Aug. 23, 2011

(54) ERROR-FREE AMPLIFICATION OF DNA FOR CLONAL SEQUENCING

(75) Inventors: Cheryl Heiner, San Mateo, CA (US); Stephen Turner, Menlo Park, CA (US); Kevin Travers, Santa Clara, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 328 days.

(21) Appl. No.: 12/286,119

(22) Filed: Sep. 26, 2008

(65) Prior Publication Data

US 2009/0105094 A1    Apr. 23, 2009

Related U.S. Application Data

(60) Provisional application No. 61/005,734, filed on Dec. 7, 2007, provisional application No. 60/995,733, filed on Sep. 28, 2007.

(51) Int. Cl.
*C12Q 1/68* (2006.01)
*C12P 19/34* (2006.01)

(52) U.S. Cl. ............... 435/6.12; 435/91.1; 435/91.2

(58) Field of Classification Search ............ 435/6, 91.1, 435/91.2
See application file for complete search history.

(56) References Cited

U.S. PATENT DOCUMENTS

| | | | |
|---|---|---|---|
| 5,001,050 A | 3/1991 | Blanco et al. |
| 5,198,543 A | 3/1993 | Blanco et al. |
| 5,547,839 A | 8/1996 | Dower et al. |
| 5,576,204 A | 11/1996 | Blanco et al. |
| 5,648,245 A | 7/1997 | Fire et al. |
| 5,674,716 A | 10/1997 | Tabor et al. |
| 5,714,320 A | 2/1998 | Kool |
| 6,210,896 B1 | 4/2001 | Chan |
| 6,255,083 B1 | 7/2001 | Williams |
| 6,261,808 B1 | 7/2001 | Auerbach |
| 6,787,308 B2 | 9/2004 | Balasubramanian |
| 6,917,726 B2 | 7/2005 | Levene et al. |
| 7,056,661 B2 | 6/2006 | Korlach et al. |
| 7,170,050 B2 | 1/2007 | Turner et al. |
| 7,476,503 B2 | 1/2009 | Turner et al. |
| 2003/0096253 A1 | 5/2003 | Nelson et al. |
| 2003/0190647 A1 | 10/2003 | Odera |

(Continued)

FOREIGN PATENT DOCUMENTS

WO    WO 91/06678 A1    5/1991

(Continued)

OTHER PUBLICATIONS

Eid et al. (2009) "Real-Time DNA Sequencing from Single Polymerase Moleculas." *Science*, 323:133-138.

(Continued)

*Primary Examiner* — Kenneth R. Horlick
(74) *Attorney, Agent, or Firm* — Quine Intellectual Property Law Group, P.C.

(57) ABSTRACT

Provided are methods of producing low copy number circularized nucleic acid variants that can be distributed to reaction volumes. The methods include providing a template nucleic acid; producing a population of clonal nucleic acids from the template nucleic acid; generating a set of partially overlapping nucleic acid fragments from the population of clonal nucleic acids; circularizing the partially overlapping nucleic acid fragments to produce circularized nucleic acid variants; and aliquotting the circularized nucleic acid variants into reaction volumes. Related compositions of nucleic acid templates are also provided.

26 Claims, 6 Drawing Sheets

U.S. PATENT DOCUMENTS

| | | |
|---|---|---|
| 2003/0215862 A1 | 11/2003 | Parce et al. |
| 2004/0048300 A1 | 3/2004 | Sood et al. |
| 2004/0152119 A1 | 8/2004 | Sood et al. |
| 2004/0224319 A1 | 11/2004 | Sood et al. |
| 2004/0259082 A1 | 12/2004 | Williams |
| 2007/0072208 A1* | 3/2007 | Drmanac .................... 435/6 |
| 2007/0099208 A1* | 5/2007 | Drmanac et al. ............. 435/6 |

FOREIGN PATENT DOCUMENTS

| | | |
|---|---|---|
| WO | WO 96/27025 A1 | 9/1996 |
| WO | WO 99/05315 A2 | 2/1999 |
| WO | WO 2006/003721 A1 | 1/2006 |
| WO | WO 2006/063355 A2 | 6/2006 |
| WO | WO 2006/138257 A2 | 12/2006 |

OTHER PUBLICATIONS

Hirsch (2002) "Functionalization of Single-Walled Carbon Nanotubes." *Angewandte Chemie International Ed.*, 11: 1853-1859.

Levene et al. (2003) "Zero-Mode Waveguides for Single-Molecule Analysis at High Concentrations." *Science*, 299(5607): 682-686.

Travers et al. (2010) "A flexable and efficient template format for circular consensus sequencing and SNP detection." *Nucleic Acids Research*, 38(15): 3159.

* cited by examiner

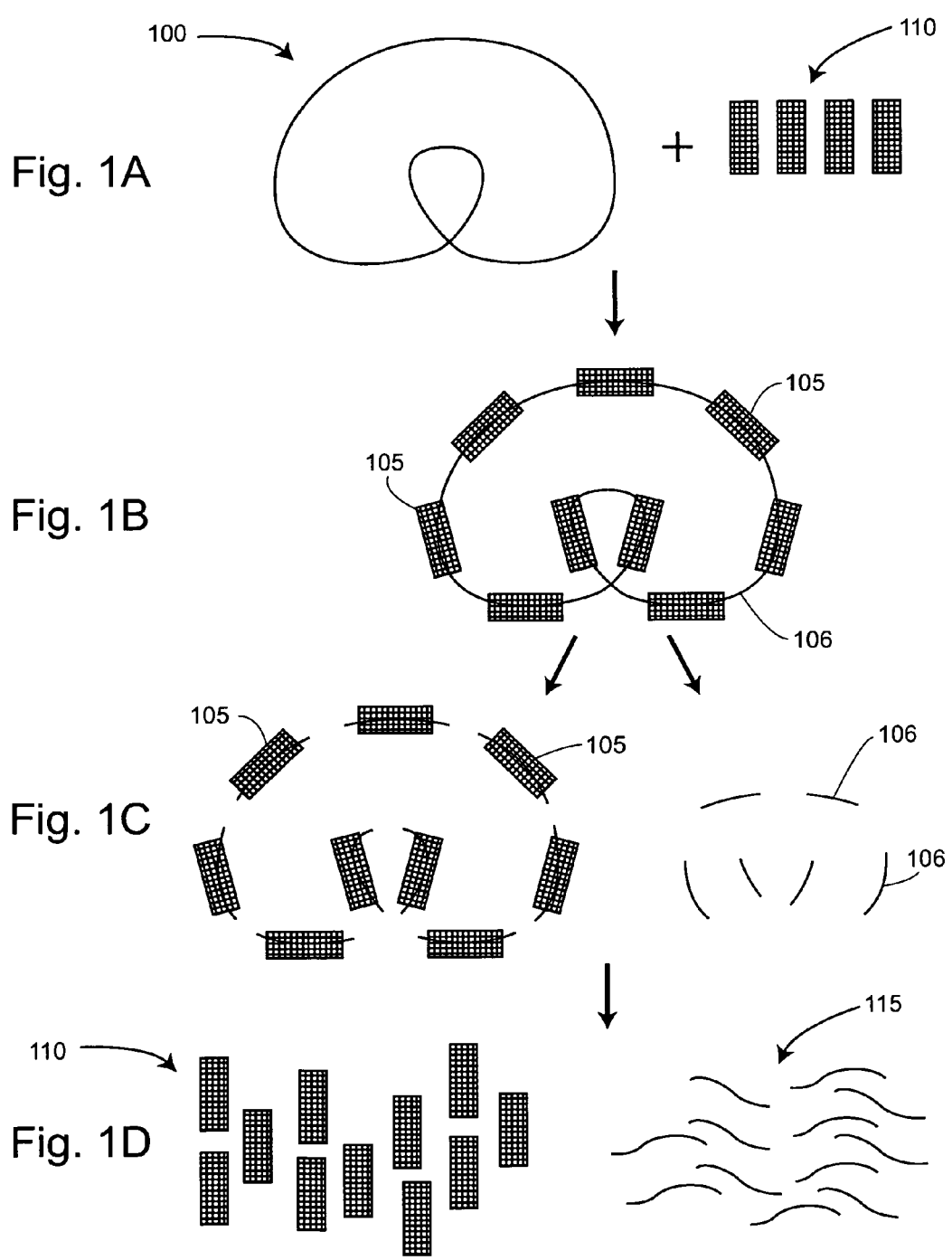

ERROR-FREE AMPLIFICATION OF DNA FOR CLONAL SEQUENCING

CROSS-REFERENCE TO RELATED APPLICATIONS

This application is related to U.S. provisional patent applications U.S. Ser. No. 60/995,733 "Error-Free Amplification of DNA for Clonal Sequencing" by Heiner and Turner, filed Sep. 28, 2007, and U.S. Ser. No. 61/005,734 "Error-Free Amplification of DNA for Clonal Sequencing" by Heiner, Turner, and Travers, filed Dec. 7, 2007, which are incorporated in their entirety for all purposes. The present application claims priority to, and benefit of, U.S. Ser. No. 60/995,733 and 61/005,734.

FIELD OF THE INVENTION

This invention is in the field of nucleic acid sequencing, particularly the preparation of templates for nucleic acid sequencing.

BACKGROUND OF THE INVENTION

The completion of Human Genome Project in 2003 (International Human Genome Sequencing Consortium (2004) "Finishing the euchromatic sequence of the human genome," Nature 431: 931-945) signaled the beginning of a new era of biomedical research and clinical practice in which biological processes could be studied in unprecedented detail. The current goals of genome research include determining the hereditary factors in disease, developing new methods to detect disease and guide therapy (van de Vijver et al. (2002) "A gene-expression signature as a predictor of survival in breast cancer," New England Journal of Medicine 347: 1999-2009), and improving the understanding of individuals' metabolisms to accelerate drug discovery. In order to pursue these goals, it will be useful for scientists and clinicians to compare the genetic heterogeneity of countless individuals' genomes. However, sequencing a single human genome can prohibitively expensive and time-consuming. The routine sequencing of individuals' genomes will become a possibility only with the availability of faster and cheaper sequencing technologies.

Sequencing approaches that substantially improve throughput at a reduced cost over classical sequencing methods have been developed. For example, zero-mode waveguides (ZMWs) are powerful new sequencing tools that facilitate detection of labeled single nucleotides into single nucleic acids (in real time) as the nucleic acids are copied by a polymerase (Levene et al. (2003) "Zero Mode Waveguides for Single Molecule Analysis at High Concentrations," Science 299: 682-686). Efficient DNA synthesis occurs only at substrate concentrations much higher than the pico- or nanomolar regime typically required by other single molecule sequencing technologies. ZMWs overcome this limitation by confining reaction volumes to the zeptoliter range, thereby enabling an inversely proportional increase in the concentrations of DNA sequencing reagents.

Current methods for preparing nucleic acid templates are not optimal for use in high throughput DNA sequencing systems. Conventional cloning and cell culture methods are time consuming and expensive. Lengthy nucleic acid purification protocols currently in use do not reliably produce nucleic acid samples that are sufficiently free of sequencing reaction inhibitors such as salt, carbohydrate and/or protein. Furthermore, these problems are magnified when such conventional techniques are scaled to the quantities that would be useful for high throughput sequencing technologies. Consequently, there is an increasing demand for efficient, low-cost methods for the preparation of high-quality nucleic acid templates. The present invention provides methods and compositions that would be useful for supplying high throughput DNA sequencing systems with such templates.

SUMMARY OF THE INVENTION

The present invention provides methods for producing circularized nucleic acid variants and distributing the circularized nucleic acid variants to low copy number reaction volumes. In methods, a set of overlapping nucleic acid fragments is generated from a population of clonal nucleic acids. The overlapping nucleic acid fragments in the set are circularized to produce circularized nucleic acid variants that comprise overlapping subsequences of at least one member of the clonal population. The circularized nucleic acid variants are then aliquoted into low copy number reaction volumes.

A method for generating the population of clonal nucleic acids from which overlapping nucleic acid fragments are to be produced is also provided. As used herein, "clonal nucleic acids" refer to the nucleic acid products that are complete or partial copies of the template nucleic acid from which they were generated. These products are substantially or completely identical to each other, and they are complementary copies of the template nucleic acid strand from which they are synthesized, assuming that the rate of nucleotide misincorporation during the synthesis of the clonal nucleic acid molecules is 0%. This method includes producing a population of nucleic acid fragments of similar lengths, attaching tags to ends of the nucleic acid fragments of similar lengths to produce tagged fragments, and amplifying the tagged fragments to generate the populations of clonal nucleic acids. Optionally, nucleic acid fragments of similar lengths can include nucleic acid fragments whose lengths are within a 20% range of one another.

One method for producing the population of nucleic acid fragments of similar lengths includes providing a template nucleic acid, binding the template nucleic acid to a plurality of single-walled carbon nanotubes (CNTs) of similar length, and cleaving a portion of the template nucleic acid that is not bound to the CNTs. The CNT-bound portion of the template nucleic acid is separated from the portion of the template nucleic acid that is not bound to the CNTs. The CNT-bound portion of the template nucleic acid is released from the CNTs to produce the population of nucleic acid fragments of similar lengths. Providing the template nucleic acid to be bound to the CNTs includes, but is not limited to, providing a genomic DNA or denaturing a genomic DNA to produce a single-stranded DNA.

Optionally, providing the template nucleic acid can comprise providing a cDNA, e.g., a cDNA derived from a tissue or a concatemer comprising a plurality of tandem short expressed sequence tags (ESTs). Other approaches for producing similar sized nucleic acid fragments include enzymatic digestion, sonication, mechanical shearing, electrochemical cleavage, nebulization, or the like.

Any of a variety of approaches can be used to attach tags to ends of nucleic acid fragments of similar lengths. As used herein, a "tag" refers to a moiety linked to a nucleic acid of interest that can be used as a molecular label to detect the nucleic acid in population and/or as a means by which to separate the nucleic acid from the population. For example, tags can be hybridized to the ends of the nucleic acid fragments and extended with a polymerase to produce tagged fragments or ligated to the ends of the nucleic acid fragments with a ligase. The ligase used to produce tagged fragments can optionally include an enzyme capable of catalyzing intermolecular ligation of single-stranded DNA molecules. Attaching tags to ends of the nucleic acid fragments optionally includes attaching tags comprising one or more moieties including a biotinylated nucleotide, a phosphorylated nucleotide, a methylated nucleotide, and the like. Tags may also include specific nucleotide sequences, such as a sequence capable of forming a hairpin secondary structure, an oligonucleotide hybridization site, a restriction site, a cis regulatory sequence, a DNA promoter, an RNA promoter, a sample or library identification tag, or the like.

Amplifying the tagged fragments to generate populations of clonal nucleic acids includes, but is not limited to, performing emulsion PCR, polony amplification, or surface amplification. The tagged fragments can be amplified an exponential rate to produce the population of clonal nucleic acids. "Amplification at an exponential rate" refers to the synthesis of nucleic acid molecules through repeated copy cycles, wherein the newly synthesized nucleic acid molecules accumulate at an approximately exponential rate during a portion of the total number of copying cycles. That is, the number of nucleic acid molecules approximately doubles after each primer extension cycle, assuming the reactions have proceeded with 100% efficiency, because each newly synthesized nucleic acid molecule can serve as a temple for the production of additional nucleic acid molecules during subsequent primer extension reactions.

However, if a nucleotide misincorporation occurs when a nucleic acid is replicated during the first cycle of an amplification reaction, all molecules produced during subsequent primer extension cycles using that nucleic acid as a template will carry this error. This is particularly true when amplifications start with very few nucleic acid molecules. As a consequence, the clonal populations of nucleic acids, though homogenous, can carry erroneous sequences. Reducing such mistakes is advantageous in generating templates for sequencing.

To reduce the rate of nucleotide misincorporation into the populations of clonal nucleic acids, the tagged fragments can be subject to rounds of linear amplification prior to being amplified at an exponential rate. "Linear amplification" refers to the synthesis of nucleic acid molecules through repeated copying cycles, wherein the newly synthesized molecules accumulate at an approximately linear rate. That is, the number of synthesized nucleic acid molecules is $t(n+1)$, where $t$ is the number of template molecules and $n$ is the number of completed copying cycles, assuming the reactions have proceeded with approximately 100% efficiency. Maintaining a linear rate of amplification is contingent upon the fact that the newly synthesized nucleic acid molecules cannot serve as templates for the production of additional nucleic acid molecules during subsequent primer extension reactions. Randomly occurring sequence errors can be reduced using this method because the errors incorporated into one nucleic acid will not be carried over into newly synthesized nucleic acids in subsequent copying cycles. Thus, lower-fidelity reaction conditions can be used during linear amplification cycles to generate populations of clonal nucleic acids, even if the tagged fragments from which the clonal nucleic acids are to be produced are present in very low copy numbers.

A set of overlapping nucleic acid fragments can be produced from a population of clonal nucleic acids in a variety of ways. For example, the population of clonal nucleic acids can be cleaved, e.g., via enzymatic digestion, sonication, mechanical shearing, electrochemical cleavage, or nebulization to produce the set of overlapping nucleic acid fragments. Another method includes copying overlapping subsequences of the population of clonal nucleic acids, e.g., by extending nested primers hybridized to interior sequences of the clonal nucleic acids with a polymerase. As used herein, "copying" refers to the process copying a template nucleic acid to generate a new nucleic acid molecule with a sequence identical to that of the template or a with a sequence complementary to that of the template. The rate of nucleotide misincorporation during the synthesis of the nucleic acid copies is assumed to be approximately 0%.

The overlapping nucleic acid fragments are circularized to generate a population of circularized nucleic acid variants comprising subsequences of at least one member of the clonal population. For example, a ligase may be used to join the two ends of each overlapping fragment. The ligase used to produce the circularized nucleic acid variants includes, but is not limited to, an enzyme capable of catalyzing intramolecular ligation of single-stranded DNA molecules, such as CircLigase™. The steps in generating the circularized nucleic acid variants are preferably performed in vitro, e.g., outside of a living organism. Optionally, these steps can all be performed in a single reaction vessel.

As used herein, "low copy number reaction volume" refers the low copy number of nucleic acid molecules in a sample. Ideally, a low copy number reaction volume will comprise a single nucleic acid molecule, but it can comprise up 1, 2, 3, 4, or up to 5 molecules. For example, aliquotting the circularized nucleic acid variants into low copy number reaction volumes comprises flowing or depositing the circularized variants onto a zero-mode waveguide. Dilution based protocols can used for delivering materials, e.g., a polymerase, a circularized nucleic acid variant, a labeled nucleotide or nucleotide analog, a divalent cation, buffer components and the like, to the ZMWs.

Thus, in one embodiment of the invention, single-stranded DNA fragments of similar lengths are provided, and tags are attached to ends the fragments with an enzyme capable of catalyzing intermolecular ligation of single-stranded DNA molecules. The tagged fragments are then amplified at a linear rate prior to being amplified at an exponential rate to produce a population of clonal nucleic acids, and the population of clonal nucleic acids is cleaved to generate a set of overlapping fragments. The two ends of each overlapping fragment are joined with an enzyme capable of catalyzing the intramolecular ligation of single-stranded DNA molecules to form circularized single-stranded DNA variants that comprise overlapping subsequences of at least one member of the clonal population of nucleic acids. The circularized single-stranded DNA variants are then flowed or otherwise deposited onto a zero-mode waveguide.

In a related aspect, the invention also provides another method for producing a set of overlapping nucleic acid fragments. In this method, a template nucleic acid, such as a genomic DNA or a genomic DNA that has been denatured to produce a single-stranded DNA, is provided. The template nucleic acid is fragmented generate a set of nucleic acid fragments, which are amplified the nucleic acid fragments to produce a population of clonal nucleic acids in vitro. The population of clonal nucleic acids is used to generate overlapping nucleic acid fragments. Previously described steps relating to fragmenting template nucleic acid, amplifying nucleic acid fragments to generate populations of clonal nucleic acids, and generating overlapping nucleic acids fragment from a population of clonal nucleic acids to produce apply to this embodiment, as well. The overlapping nucleic acid fragments produced by this method are optionally circularized using methods explicated above. Preferably, the providing and fragmenting of the template nucleic acid, the amplification of the fragments to produce clonal nucleic acids, and generating of overlapping nucleic acid fragments from the clonal population are performed in vitro. Optionally, these steps can be performed in a single reaction vessel.

The invention also provides a composition that includes a plurality of single-stranded circularized nucleic acid segments that comprise overlapping subsequences of a nucleic acid, e.g., a DNA. The composition can also include a ligase, i.e., an enzyme capable of catalyzing intramolecular ligation of single-stranded DNA molecules. In addition, the composition can optionally include a nucleotide, a nucleotide analog, a polymerase, buffer components, a cation, and the like.

Those of skill in the art will appreciate that that the methods provided by the invention for generating templates, e.g., for single molecule sequencing, e.g., in a zero mode waveguide, can be used alone or in combination with any of the compositions described herein. DNA sequencing systems that include any of the compositions described herein are also a feature of the invention. Such systems can optionally include detectors, array readers, excitation light sources, and the like.

The present invention also provides kits that that can be used to perform the methods of the invention, optionally with additional useful reagents such as one or more nucleotide analogues, e.g., for sequencing, nucleic acid amplification, or the like. Such kits can include enzymes, e.g., nucleases, ligases, polymerases, and the like, packaged in a fashion to enable a practitioner to use the methods provided by the invention. Kits can include nucleotide analogs, e.g., those that are analogous to A, T, G, and C, e.g., where one or more of the analogues comprise a detectable moiety, to permit identification in the presence of the analogues, e.g., in a sequencing reaction, e.g., performed in a zero mode waveguide. The kits of the invention optionally include additional reagents, such as buffer solutions and/or salt solutions, including, e.g., divalent metal ions, i.e., $Mg^{++}$, $Mn^{++}$ and/or $Fe^{++}$, standard solutions, e.g., dye standards for detector calibration. Such kits also typically include instructions for use of the compounds and other reagents in accordance with the desired application methods, e.g., nucleic acid sequencing, amplification and the like.

BRIEF DESCRIPTION OF THE DRAWINGS

FIG. 1 shows a schematic illustration of a carbon-nanotube-dependent method for the production of nucleic acid fragments of similar lengths.

DETAILED DESCRIPTION

Figure 2A:
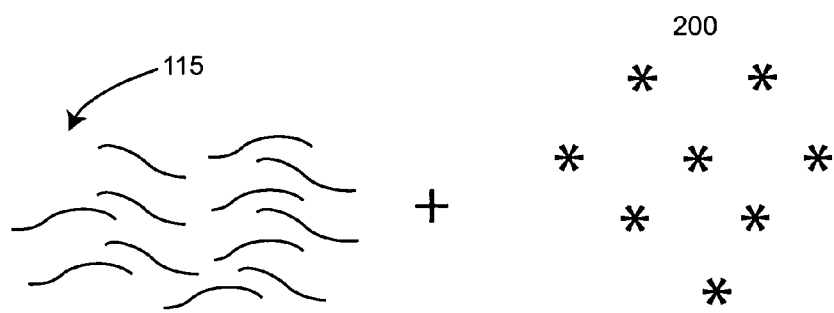
FIG. 2 illustrates a method for producing populations of clonal nucleic acids from nucleic acid fragments of similar lengths.

The present invention facilitates the preparation of nucleic acid templates and the distribution of these templates into low copy number reaction volumes. The compositions and methods provided by the invention are particularly useful for providing nucleic acid templates for sequencing to single molecule sequencing systems. Collecting reliable sequence data using such high-throughput sequencing technology depends in part on the availability of methods for the rapid and efficient production of high-quality nucleic acid templates. Furthermore, the reduction of sequencing costs from current levels is a benefit of the improved methods provided herein.

In a first aspect, the invention provides methods of preparing nucleic acid templates. In these methods, tags are linked to a population of nucleic acids of similar lengths, e.g., nucleic acid fragments whose lengths are within a 20% range of one another, to form tagged nucleic acids. These tagged nucleic acids are amplified to produce clonal populations of nucleic acids. Overlapping nucleic acid fragments are generated from the populations of clonal nucleic acids, and the two ends of each fragment are joined to form overlapping circularized nucleic acid variants of at least one member of a clonal population of nucleic acids. These circularized nucleic acid variants are then distributed to low copy number reaction volumes. Preferably, these steps are performed in vitro, to eliminate the need for a practitioner to carry out laborious and time-consuming in vivo cloning and cell culturing techniques. Another advantageous aspect of this method is that the steps related to preparing the circularized nucleic acid variants are optionally performed in a single reaction vessel, thereby decreasing costs by minimizing sample handling and reducing reagent consumption.

A preliminary step in generating nucleic acid templates, e.g., preferably between 100 nucleotides and 10,000 nucleotides long, for single-molecule sequencing is shown in FIG. 1. Nucleic acids of similar lengths, e.g., nucleic acid fragments whose lengths are within a 20% range of one another, are optionally derived from a template nucleic acid, e.g., a genomic DNA, a genomic DNA that has been denatured to produce a single-stranded genomic DNA, a cDNA derived from, e.g., a tissue, or a concatemer comprising a plurality of short expressed sequence tags. Also provided is an optional method by which a population of nucleic acids of similar lengths is generated. The method includes providing template nucleic acid 100 and binding plurality of single-walled carbon nanotubes 110 to template nucleic acid 100. The portion of the template nucleic acid that is not bound to the CNTs, e.g., portion 106, is cleaved, and CNT-bound nucleic acids 105 are separated from unbound nucleic acids 106. The CNT-bound nucleic acid fragments are released from the CNTs to produce population of nucleic acids of similar lengths 115. Other methods can also be used to produce fragments of similar lengths, e.g., enzymatic digestion, sonication, mechanical shearing, nebulization, electrochemical cleavage, or the like, optionally followed by size separation purification, e.g., chromatography, gel purification, or the like.

As shown in FIG. 2, nucleic acids of similar lengths are then tagged. Tags 200 that are linked to population of nucleic acids of similar lengths 115 are moieties that can be used as molecular labels to detect the nucleic acids to which they are linked in a population and/or as a tool with which to separate the nucleic acids to which they are linked from a population. For example, a tag optionally comprises a ligand, a modified nucleotide, a nucleotide analog, a biotinylated nucleotide, a phosphorylated nucleotide, or the like. In another aspect, a tag optionally comprises a specific nucleotide sequence, such as an oligonucleotide hybridization site, a restriction site, a cis regulatory sequence, a DNA promoter, an RNA promoter, a sample or library identification tag, or the like. The tags are optionally attached to nucleic acids of similar lengths, e.g., with a ligase, via primer extension, via chemical linkage, or the like. Optionally, a ligase used to attach tags to nucleic acids of similar lengths is capable of catalyzing intermolecular ligation of single-stranded DNA molecules.

Figure 2B:
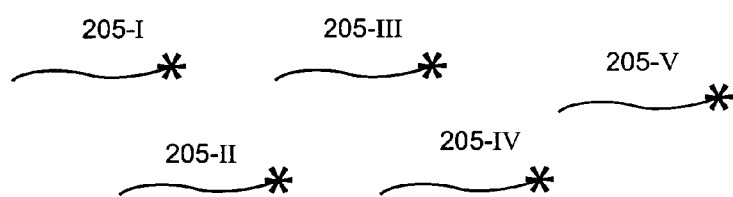
Figure 2C:
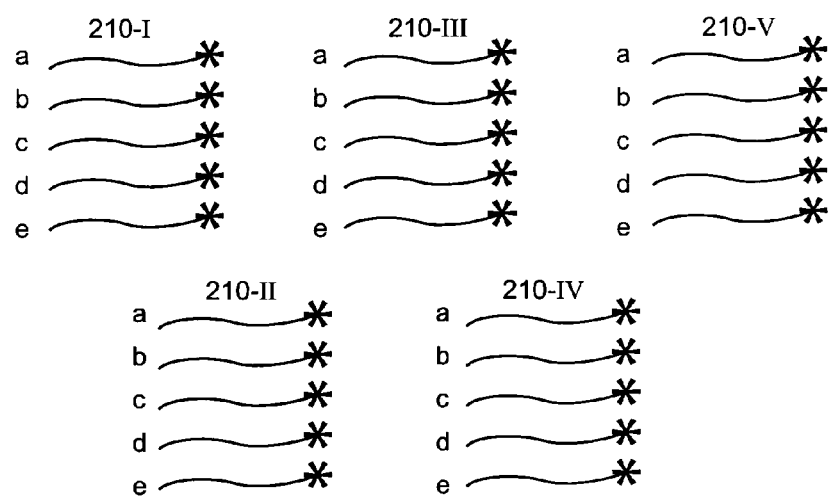

As further shown in FIGS. 2B and 2C, tagged nucleic acids of similar lengths 205I-205V are amplified to generate clonal populations of nucleic acids. The tagged nucleic acids are optionally amplified using a low-copy amplification technique, e.g., emulsion PCR, polony amplification, or surface amplification. To minimize the replication of amplification products containing nucleotide misincorporation errors, the tagged nucleic acids are optionally subject to linear amplification, i.e., the nucleic acids that are generated during repeated copying cycles accumulate at an approximately mathematically linear rate. This aspect, i.e., the reduction of nucleotide misincorporation, is of particular advantage where the templates generated from the tagged nucleic acids are to be used in single-molecule sequencing. Following several cycles of linear amplification, the amplified tagged nucleic acids are optionally subject to rounds of exponential amplification, i.e., the nucleic acid products accumulate at an approximately exponential rate after each copying cycle.

Figure 3A:
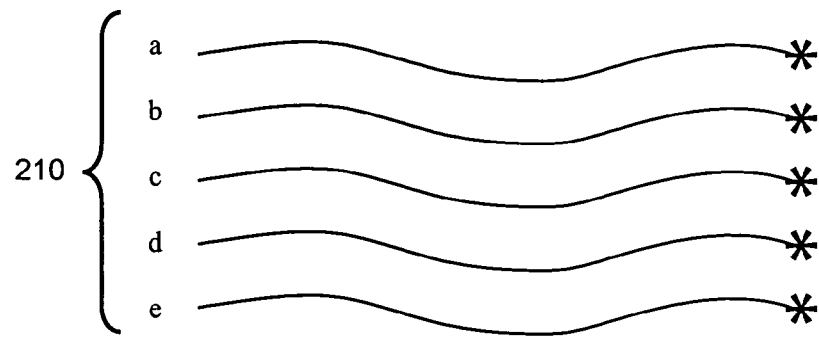
FIG. 3 shows a schematic illustration of the production of circularized nucleic acid variants from a population of clonal nucleic acids.
Figure 3B:
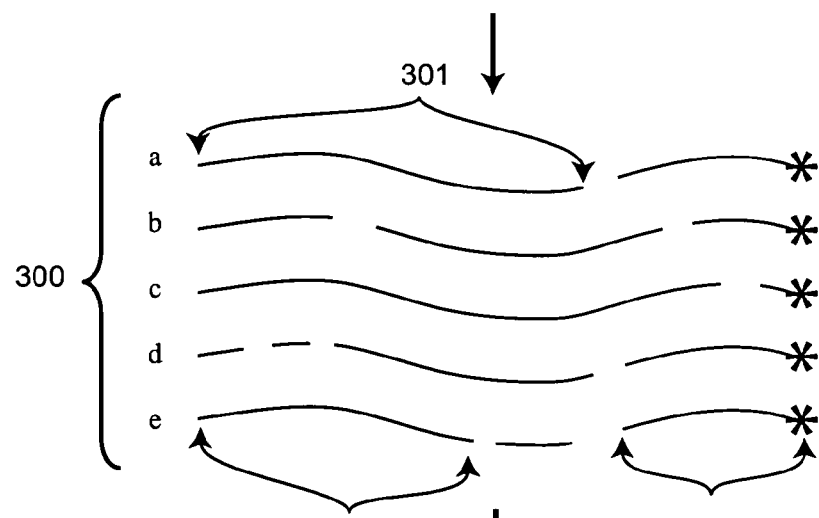
Figure 3C:
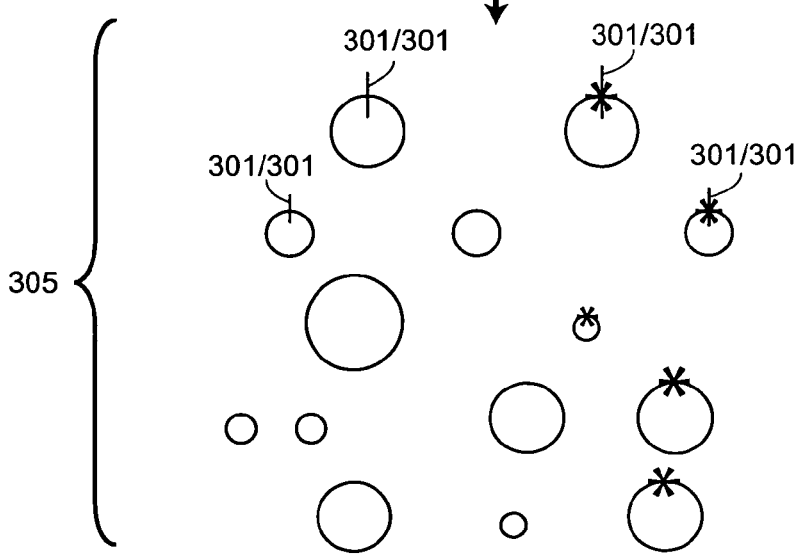
Figure 4A:
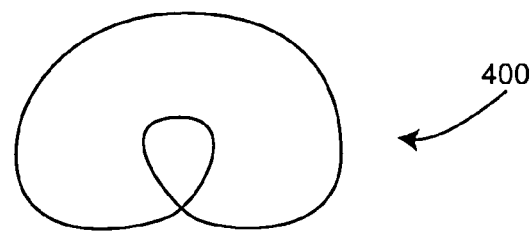
FIG. 4 illustrates a method for producing overlapping fragments from template DNA.
Figure 4B:
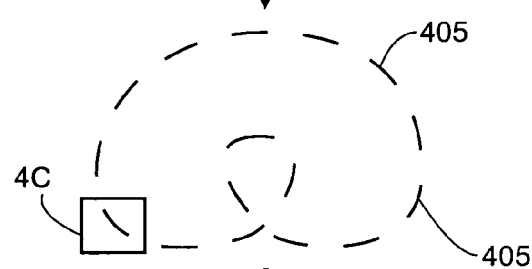
Figure 4C:
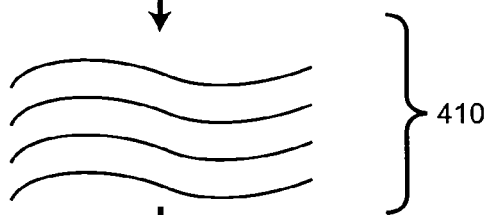
Figure 4D:
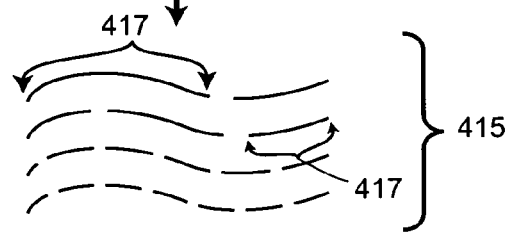
Figure 4E:
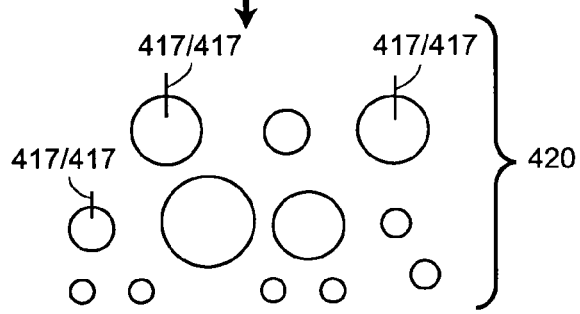

As depicted in FIG. 3, set of overlapping nucleic acid fragments 300 is generated from population of clonal nucleic acids 210. The clonal nucleic acids can be cleaved via enzymatic digestion, sonication, mechanical shearing, nebulization, electrochemical cleavage, or the like. Overlapping fragments can be generated by copying subsequences of the clonal nucleic acids, e.g., by hybridizing nested primers to the clonal nucleic acids and extending the primers with a polymerase. The two ends of fragments 301 are optionally joined using a ligase to form circularized variants 305, which comprise overlapping subsequences of at least one member of the clonal population. The circularized fragments optionally comprise DNA or single-stranded DNA. Optionally, the ligase used to join the two ends of each fragment is capable of catalyzing intramolecular ligation of single-stranded DNA molecules. The composition of circularized nucleic acid variants optionally comprises a ligase or a ligase capable of catalyzing intramolecular ligation of single stranded DNA molecules.

Figure 5:
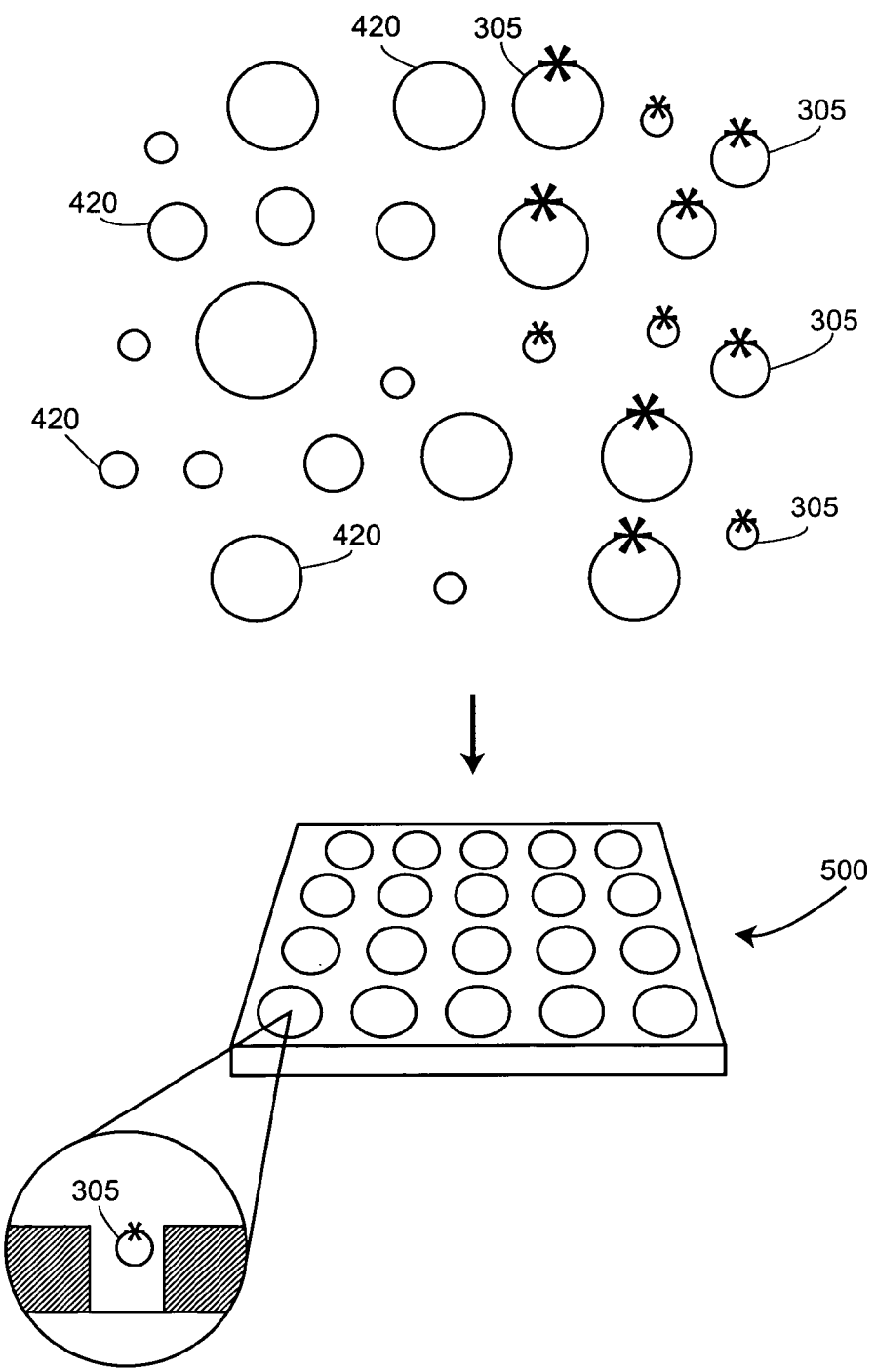
FIG. 5 depicts the aliquotting of circularized nucleic acid variants into low copy number reaction volumes.

FIG. 5 illustrates an optional distribution of circularized nucleic acids to low copy number reaction volumes in a zero-mode waveguide 500 in preparation for single-molecule sequencing analysis. For a description of ZMWs and their application in single molecule analyses, and particularly nucleic acid sequencing, see, e.g., Published U.S. Patent Application No. 2003/0044781, and U.S. Pat. No. 6,917,726, each of which is incorporated herein by reference in its entirety for all purposes. See also, Levene et al. (2003) "Zero Mode Waveguides for single Molecule Analysis at High Concentrations," *Science* 299:682-686. Ideally, a low copy number reaction volume comprises a single nucleic acid molecule, but it can comprise 2, 3, 4, or up to about 5 molecules.

The invention also provides alternative embodiments to methods of preparing nucleic acid templates and distributing them to low copy number reaction volumes for single-molecule sequencing. For example, as shown in FIG. 4, template nucleic acid 400, e.g., a genomic DNA, a genomic DNA that has been denatured to produce a single-stranded genomic DNA, a cDNA derived from, e.g., a tissue, or a concatemer comprising a plurality of short expressed sequence tags, is fragmented, and the resulting fragments 405 are amplified to generate populations of clonal nucleic acids 410. Methods that can be used to produce nucleic acid fragments 405 include enzymatic digestion, sonication, mechanical shearing, nebulization, electrochemical cleavage, or the like, as described above. Previously described steps relating to the amplification of tagged nucleic acids 205 to produce clonal nucleic acids 210 apply to the embodiment depicted in FIG. 4 as well, i.e., the same methods can be used to generate populations of clonal nucleic acids 410 from template nucleic acid fragments 405. Overlapping nucleic acid fragments 415 are prepared from a population of clonal nucleic acids by repeating any of the methods used to produce nucleic acid fragments 405 from a template nucleic acid 400, and ends 417 of each overlapping nucleic acid fragment are optionally joined with a ligase to form circularized nucleic acid variants 420. Optionally, the ligase used to join the two ends of each fragment is capable of catalyzing intramolecular ligation of single-stranded DNA molecules.

These circularized nucleic acids 420 are then distributed to low copy reaction volumes in zero mode waveguide 500, e.g., as described previously. Preferably, these steps are performed in vitro, to circumvent the need for time-consuming and labor-intensive cloning techniques. Another advantageous aspect of this invention is that the steps related to the preparation of the circularized nucleic acid variants are optionally performed in a single reaction vessel, reducing reagent usage and, thereby, reducing expense. Previously described details relating to low copy number reaction volumes apply to this embodiment, as well.

Figure 6:
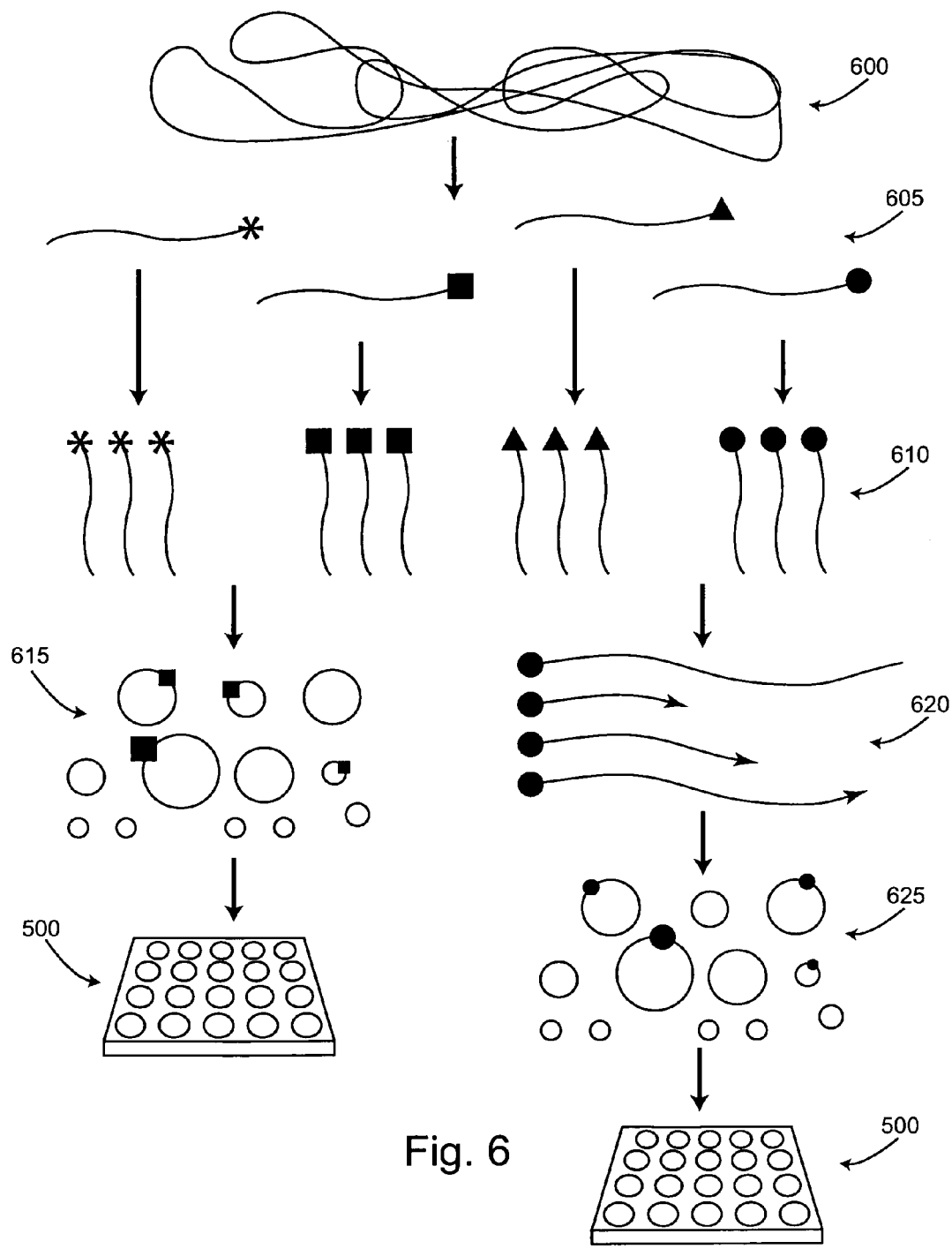
FIG. 6 depicts methods for producing circularized nucleic acid variants and providing the circularized nucleic acid variants to low copy number reaction volumes.

FIG. 6 depicts yet another embodiment for providing nucleic acid templates to low copy number reaction volumes, i.e., for single-molecule sequencing. For example, nucleic acid fragments can be prepared from a template nucleic acid 600 according to methods described above. Examples of template nucleic acids are also provided above. The fragments are tagged to form tagged fragments 605, and the tagged fragments are amplified to generate populations of clonal nucleic acids 610, using methods explicated in previous embodiments. The clonal nucleic acids are optionally fragmented and circularized to produce circularized templates 615, e.g., using methods described previously. In another aspect, clonal nucleic acids 610 are optionally copied, e.g., by hybridizing nested primers to the clonal nucleic acids and extending the primers with a polymerase. Tags are optionally attached to copied nucleic acids comprising subsequences of the population of clonal nucleic acids, and tagged copies 620 are circularized to produce circularized templates 625. The steps relating to preparing circularized fragments 615 and/or 625 are optionally performed in a single reaction vessel to reduce reagent use. The steps of this embodiment are preferably performed in vitro to avoid the need for the time-consuming cloning techniques currently used in the art. The steps explicated in previous embodiments relating to cleaving, copying, amplifying, and circularizing nucleic acid apply to the embodiment depicted in FIG. 6, as well. The circularized templates 615 and/or 625 are optionally amplified and distributed to low copy number reaction volumes, as described previously.

In a related aspect, the invention provides a sequencing system that includes compositions of circularized nucleic acid variants, a reaction chamber, and a detector configured to detect a signal from the reaction chamber. In preferred embodiments, the reaction chamber is configured to perform single-molecule sequencing reactions, in which a single nucleic acid molecule of interest is sequenced in the chamber. The signal in the system results from a transient template-dependent binding of a labeled nucleobase by a polymerase in the reaction chamber. A sequence assembly module assembles template nucleic acid sequence information based upon detection of the signal.

In one preferred embodiment, the system is configured for single molecule sequencing. For example, the reaction chamber can comprise a zero mode waveguide, configured for detection of single molecule sequencing reactions.

Most typically, the detector detects an optical signal, e.g., the detector is typically configured to detect one or more fluorescent or luminescent signal(s).

The analysis module optionally assembles nucleic acid sequence based upon detection of a plurality of signals from the reaction chamber. The signals are typically correlated to template nucleotides based upon the signal type and timing of the signals.

Of particular interest is the observation of template dependent, polymerase mediated primer extension reactions that can be monitored to identify the rate or identity of nucleotide incorporation, and thus, sequence information. See, e.g., U.S. Pat. Nos. 7,033,764, 7,052,847, 7,056,661, and 7,056,676, the full disclosures of which are incorporated herein by reference in their entirety for all purposes.

Preparing Genomic DNA

As described above, the nucleic acids that are distributed to low copy number reaction volumes in preparation for single molecule sequencing are ultimately derived from a template nucleic acid, e.g., a genomic DNA or a genomic DNA that has been denatured to form a single-stranded DNA. Genomic DNA can be prepared from any source by three steps: cell lysis, deproteinization and recovery of DNA. These steps are adapted to the demands of the application, the requested yield, purity and molecular weight of the DNA, and the amount and history of the source. Further details regarding the isolation of genomic DNA can be found in Sambrook et al., *Molecular Cloning—A Laboratory Manual* (3rd Ed.), Vol. 1-3, Cold Spring Harbor Laboratory, Cold Spring Harbor, N.Y., 2000 ("Sambrook"); and *Current Protocols in Molecular Biology*, F. M. Ausubel et al., eds., Current Protocols, a joint venture between Greene Publishing Associates, Inc. and John Wiley & Sons, Inc., (supplemented through 2007) ("Ausubel"). In addition, many kits are commercially available for the purification of genomic DNA from cells, including Wizard™ Genomic DNA Purification Kit, available from Promega; Aqua Pure™ Genomic DNA Isolation Kit, available from BioRad; Easy-DNA™ Kit, available from Invitrogen; and DnEasy™ Tissue Kit, which is available from Qiagen.

Preparing a cDNA Library

The nucleic acids that are distributed to low copy number reaction volumes in preparation for single molecule sequencing can also be derived from a cDNA library, e.g. cDNAs prepared from mRNA obtained from, e.g., a tissue. Data obtained from sequencing the nucleic acid templates derived from a cDNA library, e.g., using a ZMW, can be useful in identifying, e.g., novel splice variants of a gene of interest or in comparing the differential expression of, e.g., splice isoforms of a gene of interest, e.g., between different tissue types, between different treatments to the same tissue type or between different developmental stages of the same tissue type.

mRNA can typically be isolated from almost any source using protocols and methods described in, e.g., Sambrook et al., *Molecular Cloning—A Laboratory Manual* (3rd Ed.), Vol. 1-3, Cold Spring Harbor Laboratory, Cold Spring Harbor, N.Y., 2000 ("Sambrook"); and *Current Protocols in Molecular Biology*, F. M. Ausubel et al., eds., Current Protocols, a joint venture between Greene Publishing Associates, Inc. and John Wiley & Sons, Inc., (supplemented through 2007) ("Ausubel"). The yield and quality of the isolated mRNA can depend on how a tissue is stored prior to RNA extraction, the means by which the tissue is disrupted during RNA extraction, or on the type of tissue from which the RNA is extracted, and RNA isolation protocols can be optimized accordingly. Many mRNA isolation kits are commercially available, e.g., the mRNA-ONLY™ Prokaryotic mRNA Isolation Kit and the mRNA-ONLY™ Eukaryotic mRNA Isolation Kit (Epicentre Biotechnologies), the FastTrack 2.0 mRNA Isolation Kit (Invitrogen), and the Easy-mRNA Kit (BioChain). In addition, mRNA from various sources, e.g., bovine, mouse, and human, and tissues, e.g. brain, blood, and heart, is commercially available from, e.g., BioChain (Hayward, Calif.), Ambion (Austin, Tex.), and Clontech (Mountainview, Calif.).

Once the purified mRNA is recovered, reverse transcriptase is used to generate cDNAs from the mRNA templates. Methods and protocols for the production of cDNA from mRNAs, e.g., harvested from prokaryotes as well as eukaryotes, are elaborated in *cDNA Library Protocols*, I. G. Cowell, et al., eds., Humana Press, New Jersey, 1997, Sambrook et al., *Molecular Cloning—A Laboratory Manual* (3rd Ed.), Vol. 1-3, Cold Spring Harbor Laboratory, Cold Spring Harbor, N.Y., 2000 ("Sambrook"); and *Current Protocols in Molecular Biology*, F. M. Ausubel et al., eds., Current Protocols, a joint venture between Greene Publishing Associates, Inc. and John Wiley & Sons, Inc., (supplemented through 2007) ("Ausubel"). In addition, many kits are commercially available for the preparation of cDNA, including the Cells-to-cDNA™ II Kit (Ambion), the RETROscript™ Kit (Ambion), the CloneMiner™ cDNA Library Construction Kit (Invitrogen), and the Universal RiboClone® cDNA Synthesis System (Promega). Many companies, e.g., Agencourt Bioscience and Clontech, offer cDNA synthesis services.

Preparing Concatamers of Tandem Short Expressed Sequence Tags (ESTs)

The nucleic acids that are distributed to low copy number reaction volumes in preparation for single molecule sequencing can also be derived from concatenated short expressed sequence tags (ESTs) prepared from, e.g., a cDNA library. A short sequence tag, e.g., 10-14 bp, can contain sufficient information to uniquely identify a transcript, provided that that the tag is obtained from a unique sequence within the transcript. Short sequence tags can be linked together to from long serial molecules that can be prepared, e.g., using the methods described herein, for sequencing, e.g., using a ZMW. Quantitation of the number of times a particular tag is observed provides the expression level of the corresponding transcript. Thus, sequencing the nucleic acid templates derived from concatenated short ESTs, e.g., using a ZMW, can be useful in analyzing global gene expression patterns of, e.g., a tissue at different developmental stages, tissues in different organs from a common genotype, common tissues of different genotypes, common tissues that have been exposed to different treatments, and the like. In addition, sequencing templates derived from concatamers of short ESTs on a ZMW can eliminate the need for a practitioner to carry out laborious and time-consuming in vivo cloning and cell culturing techniques that are common for other EST-based systems for the analysis of global gene expression, e.g. SAGE (Velculescu, et al. (1995) "Serial analysis of gene expression." *Science* 270:484-487) and TALEST (Spinella, et al (1999) "Tandem arrays ligation of expressed sequence tags (TALEST): a new method for generating global gene expression profiles." *Nucl Acid Res* 27:e22).

Preparing concatenated ESTs can comprise preparing a cDNA library, e.g., as described above in the section entitled "PREPARING A cDNA LIBRARY". Typically, the prepared cDNA can then be digested with a restriction enzyme that would be expected to cleave most transcripts at least once, e.g., a restriction enzyme with a 4-base pair recognition site. The 3'-most cDNA fragments are then captured and ligated to adapter molecules that each contain a type-II restriction site, e.g., BsgI, and a second restriction site. Digestion of the adapter-ligated cDNAs, e.g., with BsgI, produces DNA fragments that consist of the adapter itself and an additional 10-12 nucleotides of unknown cDNA sequence separated from the adapter by the restriction site originally used to digest the cDNA. The fragments can then be ligated to a second adapter containing a second restriction site at one end and degenerate overhangs, e.g., which render the second adapter compatible with all possible cDNA sequences, e.g., produced by the BsgI digestion, at the other. The resulting double-tagged DNA molecules can be digested with enzymes that recognize the restriction sites on the adapters and ligated together to form concatamers that can then be prepared, e.g., using the methods described herein, for sequencing, e.g., using a ZMW. Additional information and methods describing the preparation of concatamers comprising short ESTs can be found in, e.g., Velculescu, et al. (1995) "Serial analysis of gene expression." Science 270:484-487; Spinella, et al (1999) "Tandem arrays ligation of expressed sequence tags (TALEST): a new method for generating global gene expression profiles." *Nucl Acid Res* 27:e22; WIPO Patent Application Number WO/2004/024953; and Unneberg, et al. (2003) "Transcript identification by analysis of short sequence tags—influence of tag length, restriction site, and transcript database." *Nucl Acids Res* 31: 2217-2226.

Generating Nucleic Acid Fragments

In the embodiments of the invention described herein, nucleic acid fragments are generated from a template nucleic acid. There exist a plethora of ways of generating nucleic acid fragments from a template nucleic acid. These include, but are not limited to, mechanical methods, such as sonication, mechanical shearing, nebulization, hydroshearing, and the like; enzymatic methods, such as exonuclease digestion, restriction endonuclease digestion, and the like; and electrochemical cleavage. These methods are further explicated in Sambrook et al., *Molecular Cloning—A Laboratory Manual* (3rd Ed.), Vol. 1-3, Cold Spring Harbor Laboratory, Cold Spring Harbor, N.Y., 2000 ("Sambrook"); and *Current Protocols in Molecular Biology*, F. M. Ausubel et al., eds., Current Protocols, a joint venture between Greene Publishing Associates, Inc. and John Wiley & Sons, Inc., (supplemented through 2007) ("Ausubel").

Nucleic Acid Tags

In the methods and compositions provided by this invention, nucleic acid fragments are tagged so that they can be detected in a population and/or so that they can be separated from a population. Nucleic acid tags can comprise any of a plethora of ligands, such as high-affinity DNA-binding proteins; modified nucleotides, such as methylated, biotinylated, or fluorinated nucleotides; and nucleotide analogs, such as dye-labeled nucleotides, non-hydrolysable nucleotides, or nucleotides comprising heavy atoms. Such reagents are widely available from a variety of vendors, including Perkin Elmer, Jena Bioscience and Sigma-Aldrich. Nucleic acid tags can also include oligonucleotides that comprise specific sequences, such as restriction sites, cis regulatory sites, nucleotide hybridization sites, protein binding sites, and the like. Such oligonucleotide tags can be custom synthesized by commercial suppliers such as Operon (Huntsville, Ala.), IDT (Coralville, Iowa) and Bioneer (Alameda, Calif.). The methods that can be used to join tags to nucleic acids of interest include chemical linkage, ligation (described below in LIGATION OF NUCLEIC ACIDS), and extension of a primer by a polymerase (described below in AMPLIFICATION AND COPYING OF NUCLEIC ACID FRAGMENTS). Further details regarding nucleic acid tags and the methods by which they are attached to nucleic acids of interest are elaborated in Sambrook et al., *Molecular Cloning—A Laboratory Manual* (3rd Ed.), Vol. 1-3, Cold Spring Harbor Laboratory, Cold Spring Harbor, N.Y., 2000 ("Sambrook"); and *Current Protocols in Molecular Biology*, F. M. Ausubel et al., eds., Current Protocols, a joint venture between Greene Publishing Associates, Inc. and John Wiley & Sons, Inc., (supplemented through 2007) ("Ausubel").

Ligation of Nucleic Acids

Each of the embodiments of the invention describe optional ligation steps in which tags are joined to nucleic acid fragments and/or in which nucleic acids fragments are circularized to generate the templates that will be distributed to low copy number reaction volumes. Ligation is a method by which DNAs, RNAs, or DNAs and RNAs are joined with a covalent bond. Ligations are performed by incubating the nucleic acid fragments to be joined in the presence of buffer, rATP, and a ligase enzyme capable of catalyzing the ligation reaction of interest. Further details regarding these techniques can be found in Sambrook et al., *Molecular Cloning—A Laboratory Manual* (3rd Ed.), Vol. 1-3, Cold Spring Harbor Laboratory, Cold Spring Harbor, N.Y., 2000 ("Sambrook"); and *Current Protocols in Molecular Biology*, F. M. Ausubel et al., eds., Current Protocols, a joint venture between Greene Publishing Associates, Inc. and John Wiley & Sons, Inc., (supplemented through 2007) ("Ausubel"). Furthermore, a plethora of enzymes, each capable of catalyzing a unique type of ligation reaction, are commercially available. For example, CircLigase™, from Epicentre Biotechnologies, is capable of catalyzing the intramolecular ligation of single-stranded DNA fragments; T4 RNA ligase 1, available from New England Biosciences, is capable of ligating single-stranded RNAs to other single-stranded RNAs and single-stranded RNAs to single-stranded DNAs; and T4 DNA ligase, available from many commercial sources, is capable of catalyzing both inter- and intramolecular ligation of double-stranded DNAs.

CircLigase™ is a thermostable ATP-dependent ligase that catalyzes intramolecular ligation (i.e., circularization) of single-stranded DNA templates having a 5'-phosphate and a 3'-hydroxyl group. In contrast to T4 DNA ligase, which ligates DNA ends that are annealed adjacently to each other on a complementary DNA sequence, CircLigase™ ligates ends of single-stranded DNA in the absence of a complementary sequence. The enzyme is therefore useful for making circular single-stranded DNA molecules from linear single-stranded DNA. Linear single stranded DNA molecules of 30 nucleotides in length or longer can be circularized by CircLigase™. To circularize single-stranded DNA, the single-stranded DNA, buffer, ATP, and CircLigase™ are mixed and incubated, e.g., at 60° C. for 60 minutes. Standard reaction conditions for CircLigase™ can also include the addition of $MnCl_2$ in ligation reactions where short single-stranded DNAs are to be circularized.

Amplification and Copying of Nucleic Acid Fragments

Each embodiment of the invention recites optional steps in which populations of clonal nucleic acids are amplified from nucleic acid fragment and/or in which nucleic acid fragments are generated by copying subsequences of a template nucleic acid. A variety of nucleic acid amplification and/or copying methods are known in the art and can be implemented to perform these steps. The most widely used in vitro technique among these methods is polymerase chain reaction (PCR), which requires the addition of nucleotides, oligonucleotide primers, buffer, and an appropriate polymerase to the amplification reaction mix. Additional methods that can be used to amplify, or copy, nucleic acids include strand displacement amplification (SDA), rolling-circle amplification (RCA) and multiple-displacement amplification (MDA). Each of these techniques is further described in Sambrook et al., *Molecular Cloning—A Laboratory Manual* (3rd Ed.), Vol. 1-3, Cold Spring Harbor Laboratory, Cold Spring Harbor, N.Y., 2000 ("Sambrook"); and *Current Protocols in Molecular Biology*, F. M. Ausubel et al., eds., Current Protocols, a joint venture between Greene Publishing Associates, Inc. and John Wiley & Sons, Inc., (supplemented through 2007) ("Ausubel"), and DNA Amplification: Current Technologies and Applications, V. V. Demidov et al., eds., (1st Ed.), Taylor and Francis, 2004.

Distribution of Nucleic Acid Samples to Low Copy Number Reaction Volumes in a Zero-Mode Waveguide In many cases, ZMWs are provided in arrays of 10, 100, 1000, 10,000 or more waveguides. As such, dilution based protocols can be used for delivering materials, e.g., a polymerase, a circularized nucleic acid, a labeled nucleotide or nucleotide analog, a divalent cation, buffer components and the like, to the ZMWs, producing some ZMWs that are not occupied by an enzyme or other sequencing reagent (or both), but generally resulting in the majority of occupied ZMWs (those having at least one enzyme or nucleic acid molecule immobilized therein) having only one or the otherwise desired small number, of enzymes and nucleic acids located therein. In particular, in the case of ZMWs having polymerases and nucleic acids located therein, typically, more than 50% of the occupied ZMWs have a single enzyme and nucleic acid located therein, preferably, greater than 75%, and more preferably greater than about 90% and even greater than 95% of the occupied ZMWs will have the desired number of sequencing reagent molecules, which in particularly preferred aspects will be one, but can be two, three or up to ten molecules of a given type, e.g., polymerase molecules and/or nucleic acid molecules.

In a preferred aspect, polymerases are immobilized within reaction chambers of a ZMW. These immobilized polymerases are used in single molecule sequencing reactions to sequence nucleic acid templates prepared according to the present invention. A variety of polymerases adapted to single molecule sequencing reactions have been developed, including mutant forms that display the ability to incorporate labeled nucleotides (see, e.g., Hanzel et al. POLYMERASES FOR NUCLEOTIDE ANALOGUE INCORPORATION, WO 2007/076057), and polymerases that are active when bound to surfaces (useful in single molecule sequencing reactions in which the enzyme is fixed to a surface, e.g., conducted in a zero mode waveguide; see Hanzel et al. ACTIVE SURFACE COUPLED POLYMERASES, WO 2007/075987 and Hanzel et al. PROTEIN ENGINEERING STRATEGIES TO OPTIMIZE ACTIVITY OF SURFACE ATTACHED PROTEINS, WO 2007/075873). Similarly, available modified polymerases that can incorporate labeled nucleotides can provide the enzymes of the invention, after intrinsic or extrinsic modification. For example, DNA polymerase mutants have been identified that have improved nucleotide analogue binding relative to wild-type counterpart enzymes. For example, Vent$^{A488L}$ DNA polymerase can incorporate (and, thus, sample) certain non-standard nucleotides with a higher efficiency than native Vent DNA polymerase. See Gardner et al. (2004) "Comparative Kinetics of Nucleotide Analog Incorporation by Vent DNA Polymerase" *J. Biol. Chem.*, 279: 11834-11842; Gardner and Jack "Determinants of nucleotide sugar recognition in an archaeon DNA polymerase" *Nucleic Acids Research*, 27:2545-2553.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually and separately indicated to be incorporated by reference for all purposes.

What is claimed is:

1. A method of providing low copy number circularized nucleic acid variants to reaction volumes, the method comprising:
   (a) providing a population of clonal nucleic acids;
   (b) generating a set of partially overlapping nucleic acid fragments from the population of clonal nucleic acids;
   (c) circularizing the set of partially overlapping nucleic acid fragments to produce circularized nucleic acid variants of at least one member of the clonal population, the variants comprising partially overlapping subsequences of the member; and,
   (d) aliquotting the circularized nucleic acid variants into low copy number reaction volumes.

2. The method of claim 1, wherein (a) comprises:
   producing a population of nucleic acid fragments of similar lengths;
   attaching tags to ends of the nucleic acid fragments of similar lengths to produce tagged fragments; and,
   amplifying the tagged fragments to generate the population of clonal nucleic acids.

3. The method of claim 2, wherein producing the population of nucleic acid fragments of similar lengths comprises providing a population of nucleic acids whose lengths are within a 20% range of one another.

4. The method of claim 1, wherein providing the population of clonal nucleic acids comprises providing a genomic DNA.

5. The method of claim 4, wherein the genomic DNA has been denatured to produce a single-stranded DNA.

6. The method of claim 1, wherein the population of clonal nucleic acids comprises a concatamer that comprises a plurality of tandem short expressed sequence tags (ESTs).

7. The method of claim 2, wherein attaching tags to ends of nucleic acid fragments comprises hybridizing the tags to the ends of the nucleic acid fragments and extending the tags with a polymerase to produce tagged fragments.

8. The method of claim 2, wherein attaching tags to ends of the nucleic acid fragments comprises ligating the tags to the ends of the nucleic acid fragments with a ligase to produce tagged fragments.

9. The method of claim 8, wherein the ligase, which ligates the tags to the ends of the nucleic acid fragments, comprises an enzyme capable of catalyzing intermolecular ligation of single-stranded DNA molecules.

10. The method of claim 2, wherein attaching tags to ends of the nucleic acid fragments comprises attaching tags comprising one or more moieties selected from: a biotinylated nucleotide, a phosphorylated nucleotide, a methylated nucleotide, a sequence capable of forming a hairpin secondary structure, an oligonucleotide hybridization site, a restriction site, a DNA promoter, an RNA promoter, a sample or library identification tag, and a cis regulatory sequence to the ends of the nucleic acid fragments, thereby forming tagged fragments.

11. The method of claim 2, wherein amplifying the tagged fragments comprises performing: PCR, emulsion PCR, polony amplification, or surface amplification to produce the population of clonal nucleic acids.

12. The method of claim 2, wherein amplifying the tagged fragments comprises amplifying the tagged fragments at an exponential rate to produce the population of clonal nucleic acids.

13. The method of claim 12, wherein amplifying the tagged fragments comprises linear amplification of the tagged fragments prior to amplifying the tagged fragments at an exponential rate, which linear amplification results in a reduction of nucleotide misincorporation as compared to exponential amplification alone, to produce the population of clonal nucleic acids.

14. The method of claim 1, wherein (b) comprises cleaving the population of clonal nucleic acids to produce the set of partially overlapping nucleic acid fragments.

15. The method of claim 14, wherein cleaving the population of clonal nucleic acids comprises: enzymatic digestion, sonication, mechanical shearing, electrochemical cleavage, or nebulization to produce the set of partially overlapping nucleic acid fragments.

16. The method of claim 1, wherein (b) comprises copying partially overlapping subsequences of the population of clonal nucleic acids to produce the set of partially overlapping nucleic acid fragments.

17. The method of claim 16, wherein copying partially overlapping subsequences of the population of clonal nucleic acids comprises extending nested primers, which nested primers hybridize to interior sequences of the clonal nucleic acids, with a polymerase to produce the set of partially overlapping nucleic acid fragments.

18. The method of claim 1, wherein (c) comprises ligating a first end of a fragment to a second end of the fragment with a ligase to produce circularized variants.

19. The method of claim 18, wherein the ligase which ligates a first end of a fragment to a second end of the fragment to produce circularized variants comprises an enzyme capable of catalyzing intramolecular ligation of single-stranded DNA molecules.

20. The method of claim 1, wherein aliquotting the circularized variants into low copy number reaction volumes comprises flowing or depositing the circularized variants onto zero-mode waveguides.

21. The method of claim 1, wherein reaction volumes comprise one or more sequencing reagents selected from: a labeled nucleotide or nucleotide analog, a polymerase, and a divalent cation.

22. The method of claim 2 wherein attaching tags to ends of the nucleic acid fragments comprises attaching tags comprising at least one restriction site.

23. The method of claim 1 wherein (c) comprises ligation with a ligase to produce circularized variants.

24. The method of claim 1, further comprising (e) determining the nucleic acid sequence of one or more of the circularized nucleic acid variants within the low copy number reaction volume.

25. The method of claim 24 wherein the sequence is determined using single-molecule sequencing.

26. The method of claim 1 wherein at least some of the low copy number volumes comprise a single circularized nucleic acid variant.

* * * * *